(12) United States Patent
Ajiki et al.

(10) Patent No.: US 10,022,289 B2
(45) Date of Patent: Jul. 17, 2018

(54) MASSAGING APPARATUS AND MASSAGE METHOD

(71) Applicant: Panasonic Intellectual Property Management Co., Ltd., Osaka (JP)

(72) Inventors: Kaori Ajiki, Osaka (JP); Toshimitsu Minowa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 235 days.

(21) Appl. No.: 14/597,267

(22) Filed: Jan. 15, 2015

(65) Prior Publication Data
US 2015/0216758 A1 Aug. 6, 2015

(30) Foreign Application Priority Data

Jan. 31, 2014 (JP) .................................. 2014-017111

(51) Int. Cl.
*A61H 7/00* (2006.01)
*A61H 23/02* (2006.01)
*A61N 1/32* (2006.01)

(52) U.S. Cl.
CPC ............. *A61H 7/001* (2013.01); *A61H 7/007* (2013.01); *A61H 23/0245* (2013.01);
(Continued)

(58) Field of Classification Search
CPC .......... A61H 7/00–7/001; A61H 13/00; A61H 23/00; A61H 23/02; A61H 23/0245; A61H 2023/0209; A61H 39/002; A61H 39/007–39/02; A61H 2201/10; A61H 2201/5002–2201/5005; A61H 2201/5082;
(Continued)

(56) References Cited

U.S. PATENT DOCUMENTS 4,052,981 A * 10/1977 Bachmann ......... A61H 23/0263
601/134
8,175,713 B1 * 5/2012 Cywinski ............. A61H 39/002
607/48

(Continued)

FOREIGN PATENT DOCUMENTS

CN      101039641 A    9/2007
CN      201510644 U    6/2010
(Continued)

OTHER PUBLICATIONS

The Extended European Search Report dated Jun. 29, 2015 for the related European Patent Application No. 15151585.5.
(Continued)

*Primary Examiner* — Rachel T Sippel
(74) *Attorney, Agent, or Firm* — Greenblum & Bernstein, P.L.C.

(57) ABSTRACT

A massaging apparatus includes a sheet attachable to skin, multiple skin condition sensors, and multiple massage elements. Each of the skin condition sensors included in the sheet detects skin condition near the skin condition sensor. Each of the massage elements which is included in the sheet and which is disposed at a position corresponding to that of a corresponding one of the skin condition sensors is operated based on the detection result obtained by the skin condition sensor.

10 Claims, 12 Drawing Sheets

(52) U.S. Cl.
CPC .. *A61H 2023/0227* (2013.01); *A61H 2201/10* (2013.01); *A61H 2201/1207* (2013.01); *A61H 2201/1604* (2013.01); *A61H 2201/165* (2013.01); *A61H 2201/5002* (2013.01); *A61H 2205/022* (2013.01); *A61H 2205/106* (2013.01); *A61H 2230/085* (2013.01); *A61H 2230/208* (2013.01); *A61H 2230/255* (2013.01); *A61H 2230/505* (2013.01); *A61H 2230/605* (2013.01); *A61N 1/322* (2013.01); *A61N 1/328* (2013.01)

(58) Field of Classification Search
CPC ............... A61H 2201/5089–2201/5094; A61H 2205/022; A61H 2207/00; A61H 2209/00; A61H 2230/207–2230/208; A61H 2230/30–2230/305; A61H 2230/50–2230/505; A61H 2230/60–2230/605; A61N 1/0452; A61N 1/0456; A61N 1/0476; A61N 1/0484
See application file for complete search history.

(56) References Cited

U.S. PATENT DOCUMENTS

| | | | |
|---|---|---|---|
| 2002/0077688 A1* | 6/2002 | Kirkland | A61N 1/0452 607/142 |
| 2004/0173220 A1* | 9/2004 | Harry | A43B 3/0005 128/892 |
| 2007/0257256 A1 | 11/2007 | Kugler | |
| 2008/0200778 A1 | 8/2008 | Taskinen et al. | |
| 2008/0262327 A1 | 10/2008 | Kato | |
| 2009/0036938 A1* | 2/2009 | Shipley | A61H 9/0078 607/2 |
| 2009/0058274 A1 | 3/2009 | Yokoyama et al. | |
| 2010/0004015 A1 | 1/2010 | Nilsson et al. | |
| 2010/0004715 A1 | 1/2010 | Fahey | |
| 2010/0268130 A1* | 10/2010 | Khan | A61H 9/0078 601/46 |
| 2010/0305484 A1 | 12/2010 | Grollier et al. | |
| 2011/0118655 A1* | 5/2011 | Fassih | A61N 1/044 604/20 |
| 2011/0257463 A1* | 10/2011 | Nour | A61H 9/0078 600/16 |
| 2014/0142477 A1* | 5/2014 | Park | A61H 23/02 601/46 |

FOREIGN PATENT DOCUMENTS

| | | |
|---|---|---|
| CN | 102233156 A | 11/2011 |
| DE | 102011014624 | 9/2012 |
| JP | 3-236289 | 10/1991 |
| JP | 4-312472 | 11/1992 |
| JP | 7-051338 | 2/1995 |
| JP | 7-124216 A | 5/1995 |
| JP | 2003-332632 | 11/2003 |
| JP | 2007-300112 | 11/2007 |
| JP | 2008-279015 A | 11/2008 |
| JP | 2009-048837 | 3/2009 |
| JP | 2009-513208 A | 4/2009 |
| JP | 2011-505897 | 3/2011 |
| JP | 2013-116284 | 6/2013 |
| JP | 2013-168575 | 8/2013 |
| JP | 2015-039538 A | 3/2015 |
| KR | 100963687 B | 6/2010 |
| WO | 2006/009178 | 1/2006 |
| WO | 2006/040109 A1 | 4/2006 |
| WO | 2013/151128 | 10/2013 |

OTHER PUBLICATIONS

Satoshi Aihara et al., "Trend in Research on Organic Imaging Devices" NHK Science & Technology Research Laboratories R&D No. 132, pp. 4-11, Mar. 2012.
Takanori Kiyokura et al., "Wearable Laser Blood Flowmeter" NTT Technical Review, pp. 25-27, Nov. 2005.
English Translation of Chinese Search Report dated Nov. 1, 2017 for Chinese Patent Application No. 201510025645.5.
English Translation of Chinese Search Report dated May 15, 2018 for the Chinese Patent Application No. 201510025645.5.

* cited by examiner

| BLOCK | SKIN CONDITION SENSOR | MASSAGE ELEMENT | OPERATION PATTERN |
|---|---|---|---|
| FIRST BLOCK | FIRST TO TENTH SKIN CONDITION SENSORS | FIRST TO SIXTIETH MASSAGE ELEMENTS | PINCHING MASSAGE FROM LOWER SIDE TO UPPER SIDE |
| SECOND BLOCK | ELEVENTH TO TWENTIETH SKIN CONDITION SENSORS | SIXTY-FIRST TO ONE-HUNDRED-AND-TWENTIETH MASSAGE ELEMENTS | PINCHING MASSAGE FROM LOWER SIDE TO UPPER SIDE |
| ･･･ | ･･･ | ･･･ | ･･･ |
| LTH BLOCK | TO MTH SKIN CONDITION SENSOR | TO NTH MASSAGE ELEMENT | ･･･ |

511 512 513 514

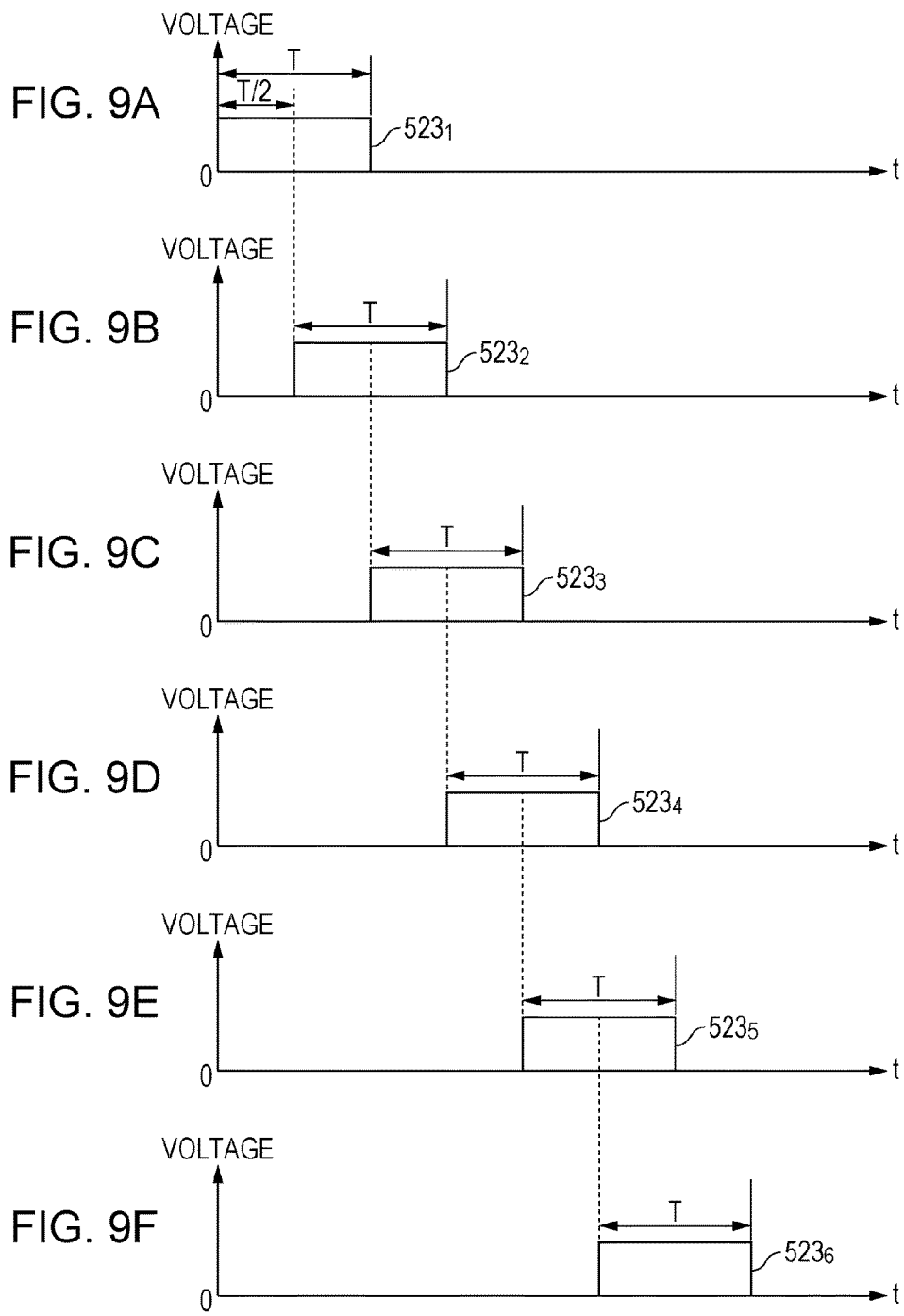

| 531 | 532 | 533 |
|---|---|---|
| OXYGEN SATURATION LEVEL | MASSAGE PATTERN | MASSAGE PATTERN INFORMATION |
| SUFFICIENT | I | · NO MASSAGES<br>ONLY CONTINUE MEASURING OXYGEN SATURATION |
| SLIGHTLY INSUFFICIENT | II | · NORMAL MASSAGE<br>THREE-CYCLE MASSAGE USING PIEZOELECTRIC ELEMENT MATRIX |
| INSUFFICIENT | III | · CAREFUL MASSAGE<br>FIVE-CYCLE MASSAGE USING PIEZOELECTRIC ELEMENT MATRIX |
| SERIOUSLY INSUFFICIENT | IV | · INTENSE MASSAGE<br>CONTINUE APPLYING MASSAGE BY USING PIEZOELECTRIC ELEMENT MATRIX, AND STOP WHEN OXYGEN SATURATION LEVEL IS IMPROVED OR WHEN TEN-CYCLE MASSAGE IS APPLIED |

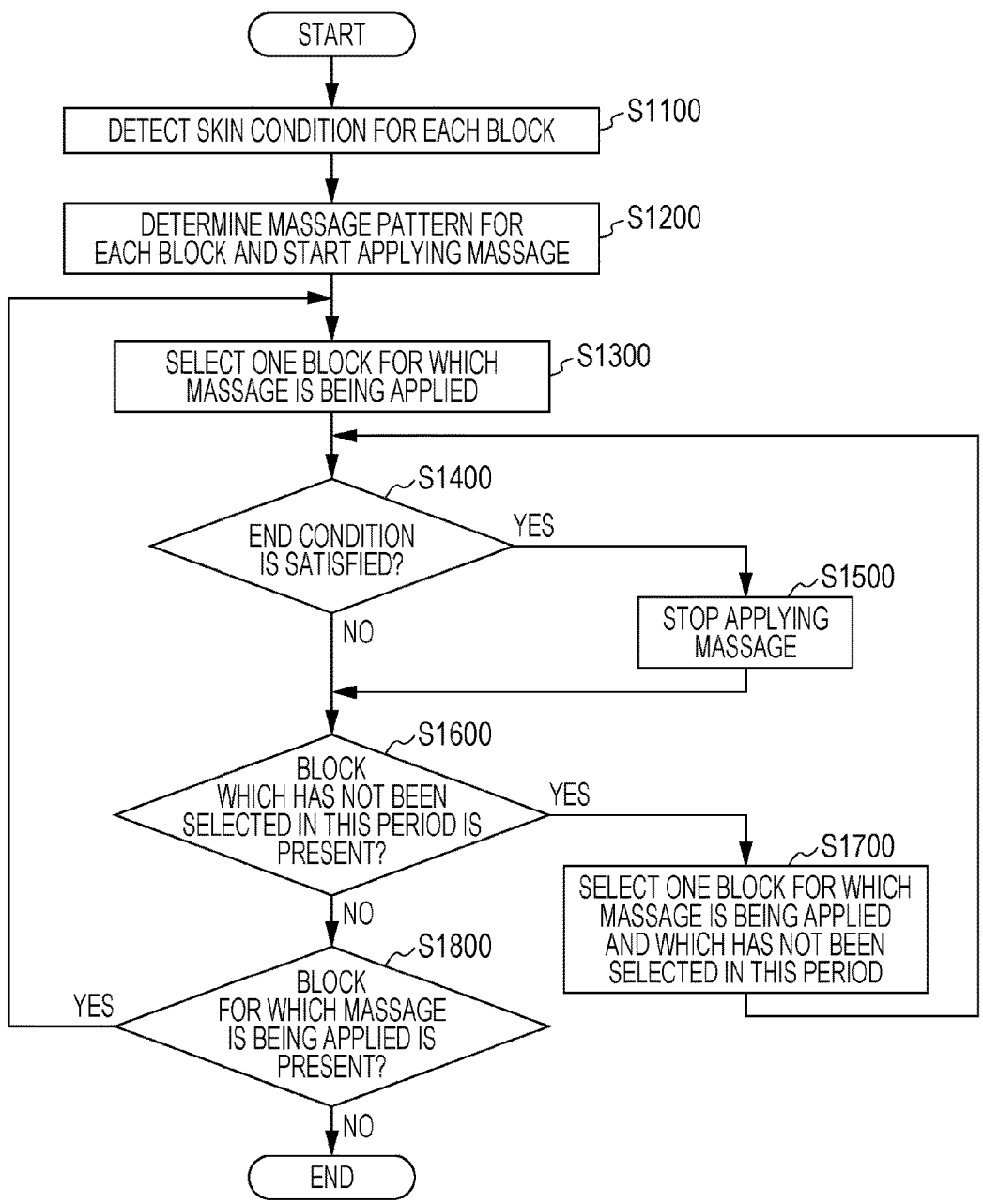

FIG. 12

| OXYGEN SATURATION LEVEL | OUTSIDE INFORMATION || MASSAGE PATTERN |
| --- | --- | --- | --- |
| | TEMPERATURE | HUMIDITY | |
| SUFFICIENT | ≥ 27°C | ≥ 80% | I |
| | | < 80% | I |
| | 20°C - 26°C | ≥ 40% | I |
| | | < 40% | II |
| | < 20°C | — | II |
| SLIGHTLY INSUFFICIENT | ≥ 27°C | ≥ 80% | I |
| | | < 80% | II |
| | 20°C - 26°C | ≥ 40% | II |
| | | < 40% | II |
| | < 20°C | — | II |
| INSUFFICIENT | ≥ 27°C | ≥ 80% | II |
| | | < 80% | II |
| | 20°C - 26°C | ≥ 40% | II |
| | | < 40% | III |
| | < 20°C | — | III |
| SERIOUSLY INSUFFICIENT | ≥ 27°C | ≥ 80% | II |
| | | < 80% | III |
| | 20°C - 26°C | ≥ 40% | III |
| | | < 40% | IV |
| | < 20°C | — | IV |

MASSAGING APPARATUS AND MASSAGE METHOD

CROSS REFERENCE TO RELATED APPLICATION

This application claims priority to Japanese Patent Application No. 2014-017111, filed on Jan. 31, 2014, the contents of which are hereby incorporated by reference.

BACKGROUND

1. Technical Field

The present disclosure relates to a massaging apparatus and a massage method.

2. Description of the Related Art

Heretofore, there have been various types of massaging apparatuses (for example, see Japanese Unexamined Patent Application Publications No. 7-51338 and No. 2013-116284). In a massaging apparatus described in Japanese Unexamined Patent Application Publication No. 7-51338, multiple massage elements are disposed in a face sheet covering the entire face, and the massage elements are operated with an operation pattern specified by a user. In a massaging apparatus described in Japanese Unexamined Patent Application Publication No. 2013-116284, multiple massage elements are disposed in a sheet of about several centimeter square.

A user wears the face sheet of the massaging apparatus described in Japanese Unexamined Patent Application Publication No. 7-51338 on his/her face. Instead, a user attaches the sheet of the massaging apparatus described in Japanese Unexamined Patent Application Publication No. 2013-116284 to skin in an area to which massage is to be applied. Thus, the technology (hereinafter referred to as "the related art") described in Japanese Unexamined Patent Application Publications No. 7-51338 and No. 2013-116284 enables flow of blood and lymph or the like to be improved by massaging skin, achieving improvement in skin condition.

However, in the related art, it is difficult to achieve improvement in skin condition efficiently.

SUMMARY

One non-limiting and exemplary embodiment provides a massaging apparatus which achieves improvement in skin condition efficiently.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a massaging apparatus including a sheet attachable to skin, a skin condition sensor included in the sheet, and a massage element included in the sheet. The massage element is operated based on a detection result obtained by the skin condition sensor.

These general and specific aspects may be implemented using a system, a method, and a computer program, and any combination of systems, methods, and computer programs.

The massaging apparatus according to the present disclosure enables improvement in skin condition to be efficiently achieved.

BRIEF DESCRIPTION OF THE DRAWINGS

FIG. 7 is a diagram illustrating an exemplary block information table according to the second embodiment;

FIGS. 9A to 9F are diagrams illustrating an exemplary operation pattern according to the second embodiment;

FIG. 10 is a diagram illustrating an exemplary control rule table according to the second embodiment;

FIG. 11 is a flowchart of an exemplary operation performed by the massaging apparatus according to the second embodiment; and FIG. 12 is a diagram illustrating another exemplary control rule table according to the second embodiment.

DETAILED DESCRIPTION

Underlying Knowledge Forming Basis of the Present Disclosure

The intensity of massage (stimulus intensity and the number of massages) which is to be applied to skin by a massaging apparatus depends on skin condition. For example, intenser massage needs for a portion in which lymph stays. In contrast, it should be avoided to excessively massage a portion having sufficiently good skin condition including the lymph flow. Therefore, to improve skin condition effectively, each portion of skin may receive a massage with adequate intensity, which is not too gentle and not too intense.

However, skin condition is typically uneven even in a narrow area such as a face. It is difficult to accurately determine which part is to undergo massage with which degree of intensity. In addition, operations of finding out a portion which needs to undergo massage, selecting an adequate operation pattern, and attaching a sheet so that the sheet covers the portion are troublesome for a user. That is, in the related art, it is difficult to improve skin condition effectively.

Embodiments of the present disclosure will be described in detail with reference to the drawings.

First Embodiment

A first embodiment of the present disclosure is an exemplary basic aspect of the present disclosure.

Figure 1:
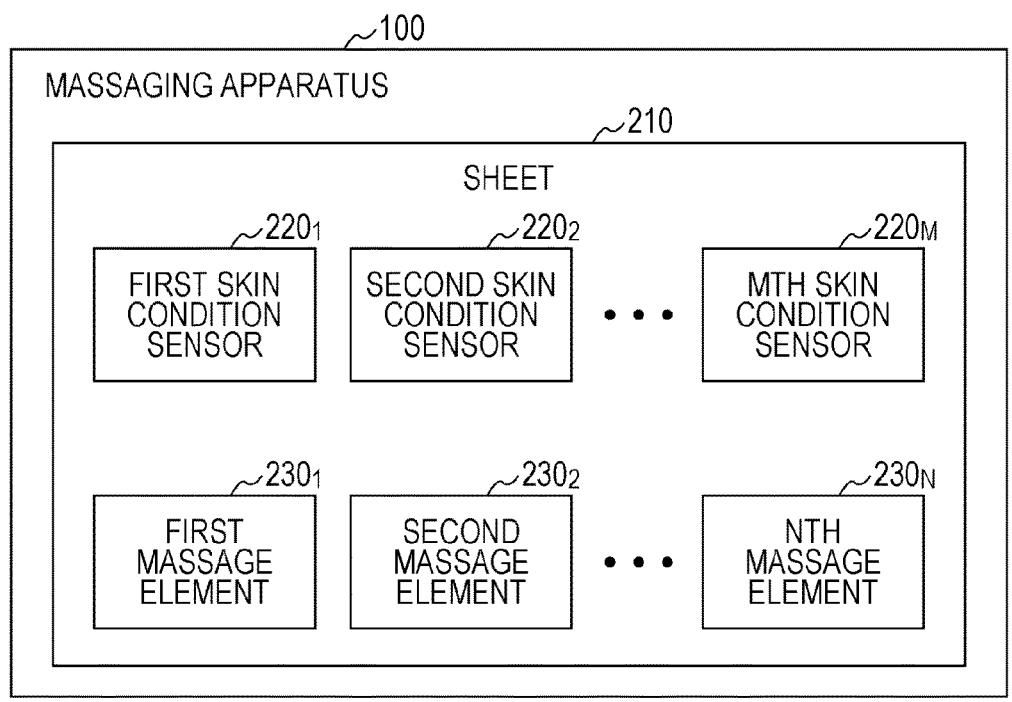
FIG. 1 is a diagram illustrating an exemplary configuration of a massaging apparatus according to a first embodiment of the present disclosure.

FIG. 1 is a diagram illustrating an exemplary configuration of a massaging apparatus according to the first embodiment.

In FIG. 1, a massaging apparatus 100 includes a sheet 210, first to Mth skin condition sensors $220_1$ to $220_M$, and first to Nth massage elements $230_1$ to $230_N$.

The sheet 210 is a member attachable to skin.

Each of the first to Mth skin condition sensors $220_1$ to $220_M$ disposed in the sheet 210 detects information related to condition of skin near the skin condition sensor 220.

Each of the first to Nth massage elements $230_1$ to $230_N$ is disposed in the sheet 210 at a position corresponding to that of a corresponding one of the first to Mth skin condition sensors $220_1$ to $220_M$. Each of the first to Nth massage elements $230_1$ to $230_N$ massages skin near the massage element 230. Each of the first to Nth massage elements $230_1$ to $230_N$ is operated in accordance with the detection result from a corresponding one of the skin condition sensors 220.

The massaging apparatus 100 having this configuration is capable of massaging each skin portion in accordance with the skin condition of the portion, achieving improvement in the skin condition efficiently.

In the massaging apparatus 100, one skin condition sensor 220, not multiple skin condition sensors 220, may be disposed in the sheet 210. In addition, one massage element 230, not multiple massage elements 230, may be disposed in the massaging apparatus 100.

Second Embodiment

A second embodiment of the present disclosure is an exemplary specific aspect of a case in which the present disclosure is applied to a face sheet which covers the entire face.

Appearance and Configuration of Massaging Apparatus

The appearance and the configuration of a massaging apparatus according to the second embodiment will be described.

Appearance of Massaging Apparatus

Figure 2:
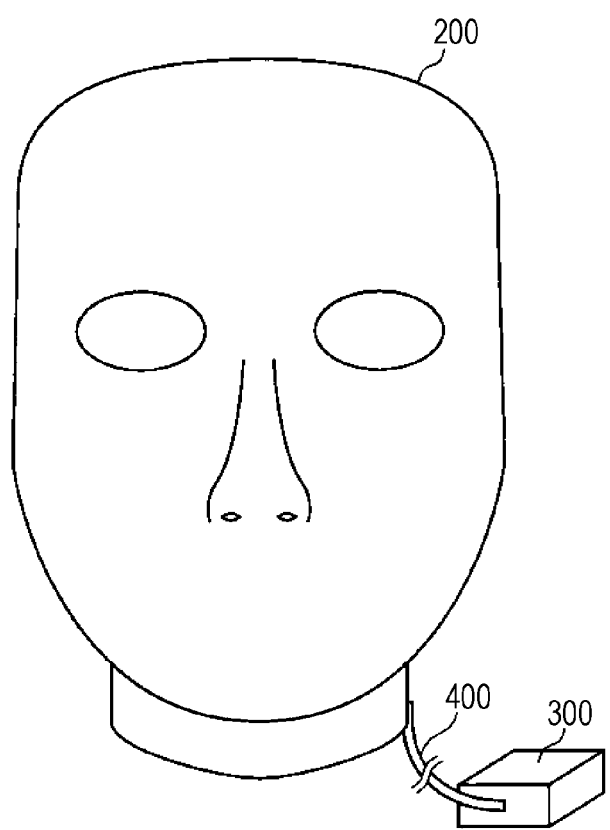
FIG. 2 is a diagram illustrating an exemplary appearance of a massaging apparatus according to a second embodiment of the present disclosure.

FIG. 2 is a diagram illustrating an exemplary appearance of the massaging apparatus according to the second embodiment.

As illustrated in FIG. 2, the massaging apparatus 100 includes a sheet device 200 and a controller 300.

The sheet device 200 having a three-dimensional shape in which the entire face surface including a portion below the chin and an upper portion of the neck is covered is a device which is formed of a sheet having elasticity and flexibility as a base material. As the sheet used as a base material, a curing material which is composed of an energy ray-curable composition containing an acryloyl group-terminated urethane polymer and an acrylic monomer and which is described, for example, in Japanese Unexamined Patent Application Publication No. 2013-168575 may be employed.

The sheet device 200 has openings in portions corresponding to the eyes and the nostrils. When the sheet device 200 is worn at a predetermined position of the face, the sheet device 200 keeps in close contact with the skin surface of the entire face due to the surface tension. To achieve sufficient close contact, an adhesive having biocompatibility, such as spirit gum, a silicon adhesive, or a latex adhesive, may be also used. A sheet device 200 may be selected from those of different sizes in accordance with the face size.

On the surface, with which the face is in close contact, of the sheet included in the sheet device 200 (hereinafter referred to as an "inner surface"), multiple skin condition sensors and multiple massage elements (not illustrated) are disposed. The detailed configuration of the sheet device 200, including the layout of the skin condition sensors and the massage elements, will be described below.

The controller 300 is an apparatus unit protected with a housing composed of a material such as plastic. As described below, the controller 300 has a function of controlling the operations of the skin condition sensors and the massage elements. The controller 300 is connected to the sheet device 200 through a cable 400.

The cable 400 includes signal lines connecting the controller 300 to each of the skin condition sensors and the massage elements (not illustrated). The cable 400 may have a length such that it is possible for the controller 300 to be put in a pocket of user clothes, for example, in a state in which the sheet device 200 is worn on the user face.

Configuration of Sheet Device

Figure 3:
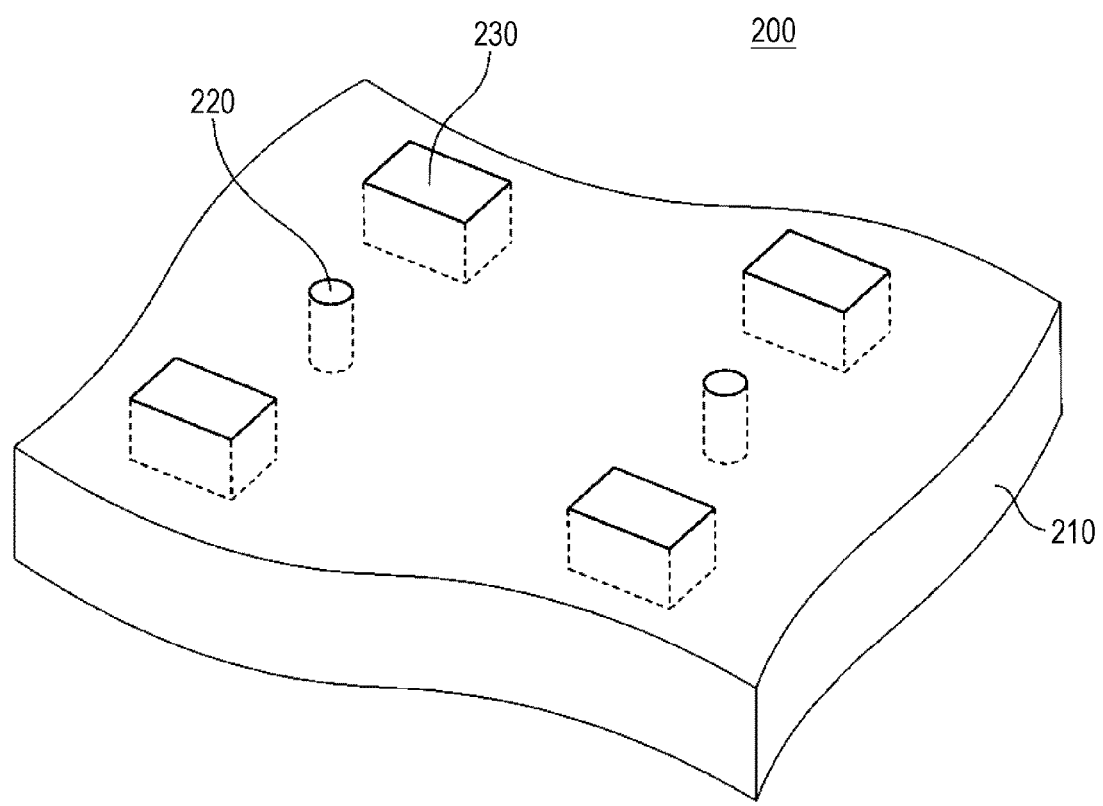
FIG. 3 is a diagram illustrating an exemplary configuration of a sheet device according to the second embodiment.

FIG. 3 is a diagram illustrating an exemplary configuration of the sheet device 200. In FIG. 3, a portion in the entire sheet device 200 is illustrated.

In FIG. 3, the sheet device 200 has a configuration in which the skin condition sensors 220 and the massage elements 230 are embedded in the sheet 210.

In a state in which the sheet device 200 is attached to skin, each of the skin condition sensors 220 detects information related to condition of skin near the skin condition sensor 220. The skin condition sensor 220 detects skin information relate to condition including at least one of a blood flow volume of skin, an oxygen saturation of skin, a tensile strength of skin, a skin temperature, a blood pressure of skin, the amount of water of skin, the amount of sebum of skin, a color tone of skin, and the degree of muscular tension under skin.

In the second embodiment, the skin condition sensor 220 is an oxygen saturation sensor that detects an oxygen saturation of blood flowing through blood capillaries under skin. The skin condition sensor 220 functioning as an oxygen saturation sensor includes a light emitting device which outputs, for example, near infrared light, and a photo detector which receives light produced by reflecting, from the skin, the light outputted from the light emitting device. A surface of the skin condition sensor 220 with which an oxygen saturation is detected (that is, a light-emitting surface and a light-receiving surface) is exposed on the surface (the upper surface in FIG. 3, and hereinafter referred to as an "inner surface") of the sheet 210, with which skin is in close contact.

As the skin condition sensor 220, an oxygen saturation sensor (biological probe) described, for example, in International Publication No. 2006/009178 may be employed. In this case, the skin condition sensor 220 obtains light information which indirectly indicates an oxygen saturation of blood, not an oxygen saturation of blood itself, and outputs it to the controller 300. The amount of light absorption of near infrared light into skin is calculated from the light information, and an oxygen saturation of blood flowing through blood capillaries under the skin is calculated from the amount of the light absorption.

For example, as described in International Publication No. 2006/009178, hemoglobin contained in blood has light absorption characteristics in a near-infrared region which differ between when the hemoglobin is combined with oxygen and when the hemoglobin is not combined with oxygen. Near infrared rays are not cut off by skin. Therefore, near infrared light is emitted to a skin surface, and the amount of light absorption of near infrared light is measured. Accordingly, an oxygen saturation of blood under skin may be measured. Oxygen saturation is highly relevant to the presence or absence of edema. For example, an oxygen saturation of less than 95% indicates abnormal blood circulation, and it is presumed that edema occurs.

In a state in which the sheet device 200 is attached to a skin portion, each of the massage elements 230 applies massage including at least one of pinching massage and electrical stimulation, to skin near the massage element 230. In the second embodiment, the massage element 230 is a massage element which applies pinching massage to skin.

Pinching massage is massage with which skin is contracted in a direction parallel to the skin surface. When skin is contracted, pressure produced by the contraction causes lymph in the skin portion to flow to a nearby skin portion. That is, pinching massage is just like massage such that skin is slightly pressed by using fingers or rollers.

The massage element 230 which applies pinching massage may be achieved, for example, by using a piezoelectric element. As the massage element 230 achieved by using a piezoelectric element, a piezoelectric element described, for example, in Japanese Unexamined Patent Application Publication No. 3-236289 may be employed. In this case, the operating surface of the massage element 230 is exposed on the inner surface of the sheet 210. The massage element 230 produces a displacement according to the voltage in synchronization with many nearby massage elements, achieving pinching massage applied to an area in which these massage elements are disposed. A pair of piezoelectric elements which contract skin may be regarded as one massage element 230.

In the second embodiment, the massaging apparatus 100 applies pinching massage in such a manner that the massage area is moved over skin in a predetermined direction. This operation is similar to that of massage such that fingers or rollers are slid over skin (massage in the horizontal direction).

To achieve fine massage, the skin condition sensor 220 and the massage element 230 may be as small as possible. To finely manufacture the piezoelectric element described in Japanese Unexamined Patent Application Publication No. 3-236289, for example, a method which is described in Japanese Unexamined Patent Application Publication No. 2003-332632 and in which fine piezoelectric elements are arranged in an array may be employed.

Unit of Control in Sheet Device

In the second embodiment, the operation of the sheet device 200 is controlled for each of divided areas obtained by dividing the sheet device 200 into multiple areas of about several to more than 10 cm. Hereinafter, each divided area of the sheet device 200 is referred to as a "block" serving as a unit of control.

Figure 4:
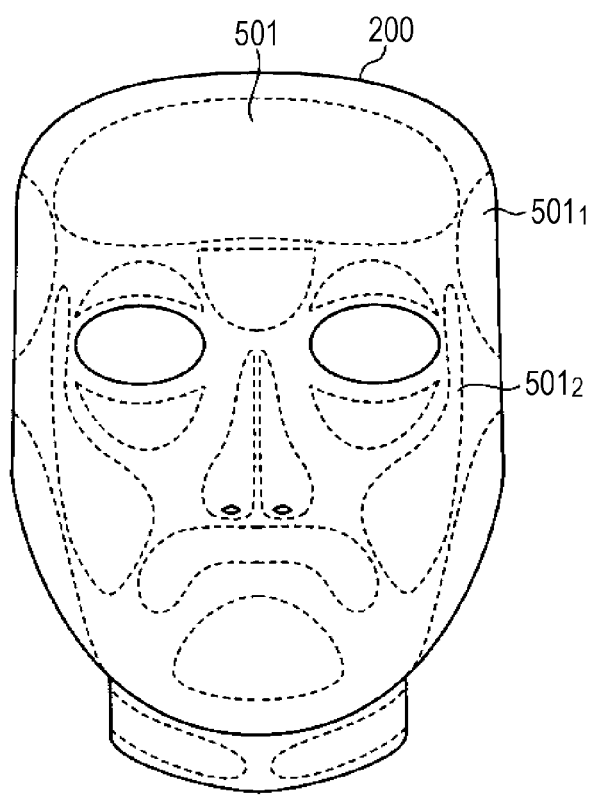
FIG. 4 is a diagram illustrating an exemplary block layout according to the second embodiment.

FIG. 4 which corresponds to FIG. 2 is a diagram illustrating an exemplary block layout of the sheet device 200.

As illustrated in FIG. 4, multiple blocks 501 corresponding to the areas obtained by dividing the entire face are set on the sheet device 200. For example, there are a block $501_1$ corresponding to the forehead and a block $501_2$ corresponding to an area from the left temple to a lower portion of the cheek bone (hereinafter referred to as a "left-cheek-bone outer portion"). Therefore, in the sheet device 200, the on/off state or the intensity of massage may be controlled separately, for example, for the forehead and the left-cheek-bone outer portion.

In the second embodiment, the blocks 501, the number of which is L, are set on the sheet device 200. Multiple skin condition sensors 220 and multiple massage elements 230 are disposed in one block 501.

Figure 5:
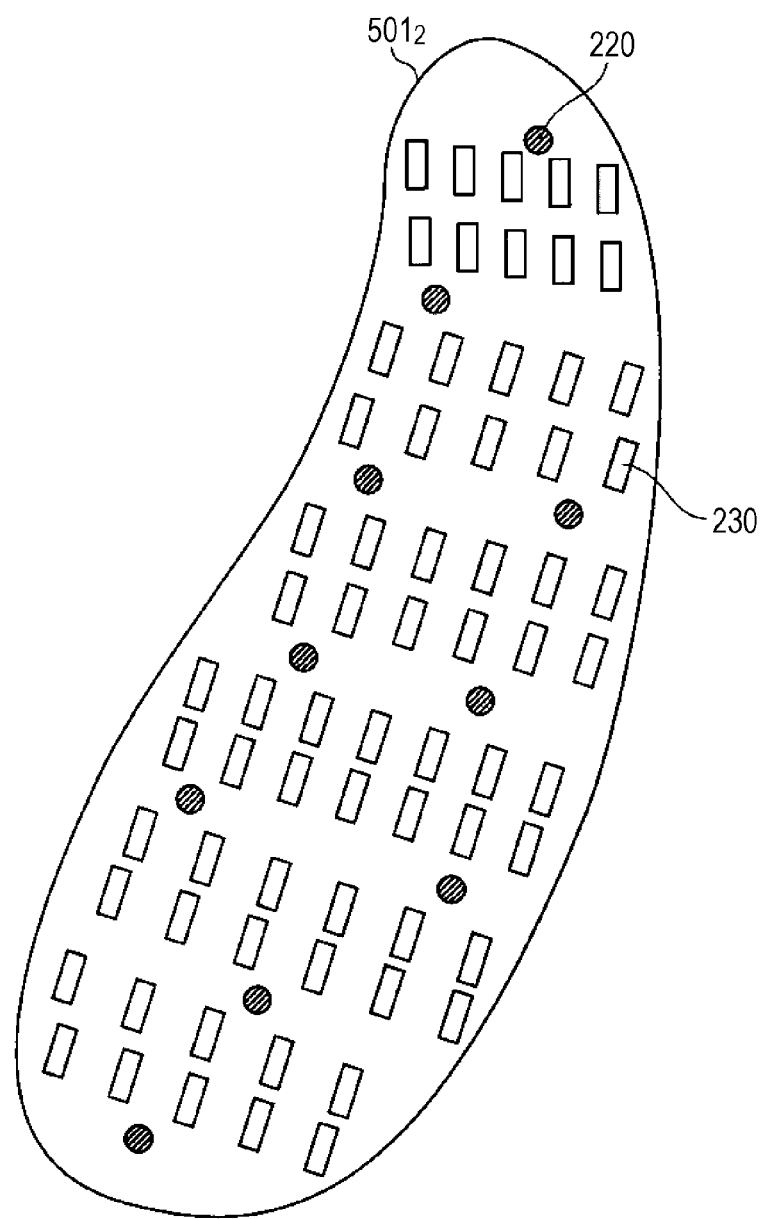
FIG. 5 is a diagram illustrating an exemplary layout of skin condition sensors and massage elements according to the second embodiment.

FIG. 5 is a diagram illustrating an exemplary layout of skin condition sensors 220 and massage elements 230 in the block $501_2$ in the left-cheek-bone outer portion.

As illustrated in FIG. 5, for example, the massage elements 230 are disposed in substantially even density over the entire block $501_2$. The skin condition sensors 220 are also disposed in substantially even density over the entire block $501_2$ among the massage elements 230.

The number of blocks 501 and the layout of the blocks 501 are not limited to the example illustrated in FIG. 4. The layout of the skin condition sensors 220 and the massage elements 230 in the block $501_2$ is not limited to the example in FIG. 5. The layout density of the skin condition sensors 220 and the massage elements 230 in the sheet device 200 may be even, may differ among blocks, or may differ among portions in a block.

Functional Configuration of Massaging Apparatus

Figure 6:
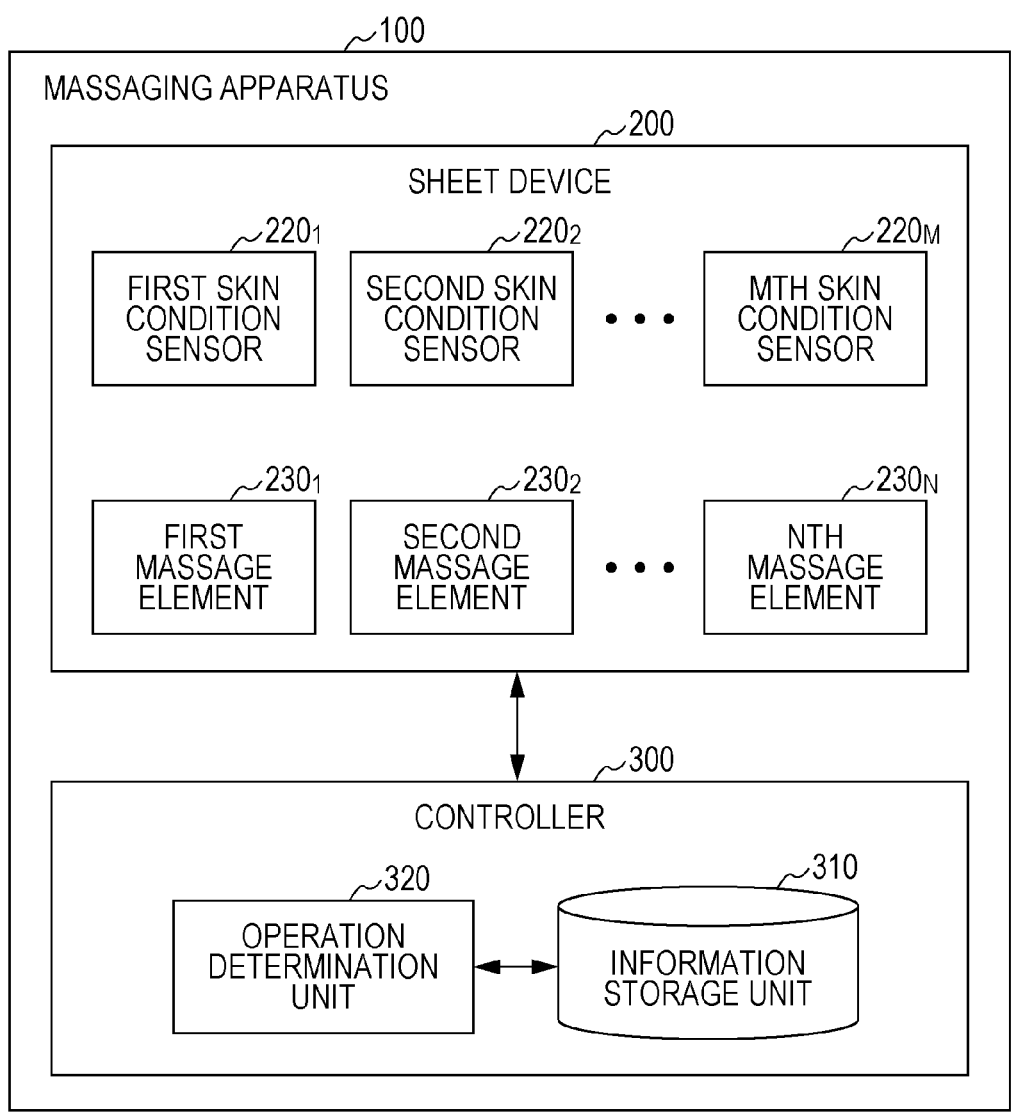
FIG. 6 is a diagram illustrating an exemplary functional configuration of the massaging apparatus.

FIG. 6 is a diagram illustrating an exemplary functional configuration of the massaging apparatus 100.

In FIG. 6, the massaging apparatus 100 includes the first to Mth skin condition sensors $220_1$ to $220_M$ and the first to Nth massage elements $230_1$ to $230_N$ which are disposed in the sheet device 200. The massaging apparatus 100 also includes an information storage unit 310 and an operation determination unit 320 which are disposed in the controller 300.

The information storage unit 310 stores a block information table and a control rule table in advance. The block information table is an association for specifying, for each of the above-described blocks 501, which skin condition sensors 220 and which massage elements 230 are disposed and which pattern with which the massage elements 230 are operated is employed when massage is applied. The control rule table is an association for specifying intensity with which massage is to be applied in accordance with skin condition.

FIG. 7 is a diagram illustrating an exemplary block information table.

As illustrated in FIG. 7, in association with block identification information 511 of a block 501, a block information table 510 describes identification information 512 of the skin condition sensors 220 disposed in the block 501 and identification information 513 of the massage elements 230 disposed in the block 501. In association with the block identification information 511, the block information table 510 also describes a pattern (hereinafter referred to as an "operation pattern") 514 employed when the massage elements 230 in the block 501 are operated.

Blood vessels and lymphatic vessels run all over under skin. Water containing nutrients oozes from a blood vessel wall so as to reach each cell. In contrast, old cells and unnecessary nutrients constitute waste products which are carried to lymphatic vessels and which are discharged through the kidneys to the outside of the body. Ninety percent of water in a body goes back to blood vessels, and the remainder of the water in the body is carried through lymphatic vessels. However, when flow of blood and lymph is hindered for some reason so that the water and the waste products are not smoothly carried, the water and the waste products excessively stay among cells (intercellular fluid). This is a reason of so-called "edema".

If edema is left untreated, the water and the waste products which are staying may combine with fat cells, leading to occurrence of enlarged fat cells ("cellulite"). The growing cellulite causes blood vessels and lymphatic vessels to be pressed, resulting in further inhibition of circulation of the water and the waste products. Therefore, edema is to be eliminated by circulating intercellular fluid through application of massage in an early stage.

The operation pattern for each of the blocks 501 in the second embodiment is set so as to improve circulation of lymph. Specifically, the operation pattern is a pattern with which an area in which the massage elements 230 apply pinching massage to skin (hereinafter referred to as a "massage area") is moved in each of the blocks 501 in a direction in which lymph under the skin is discharged (hereinafter referred to as a "lymph discharge direction").

To move the massage area, multiple areas (hereinafter referred to as "subblocks") into which an block is divided, for example, in the lymph discharge direction are set in the sheet device 200.

Figure 8:
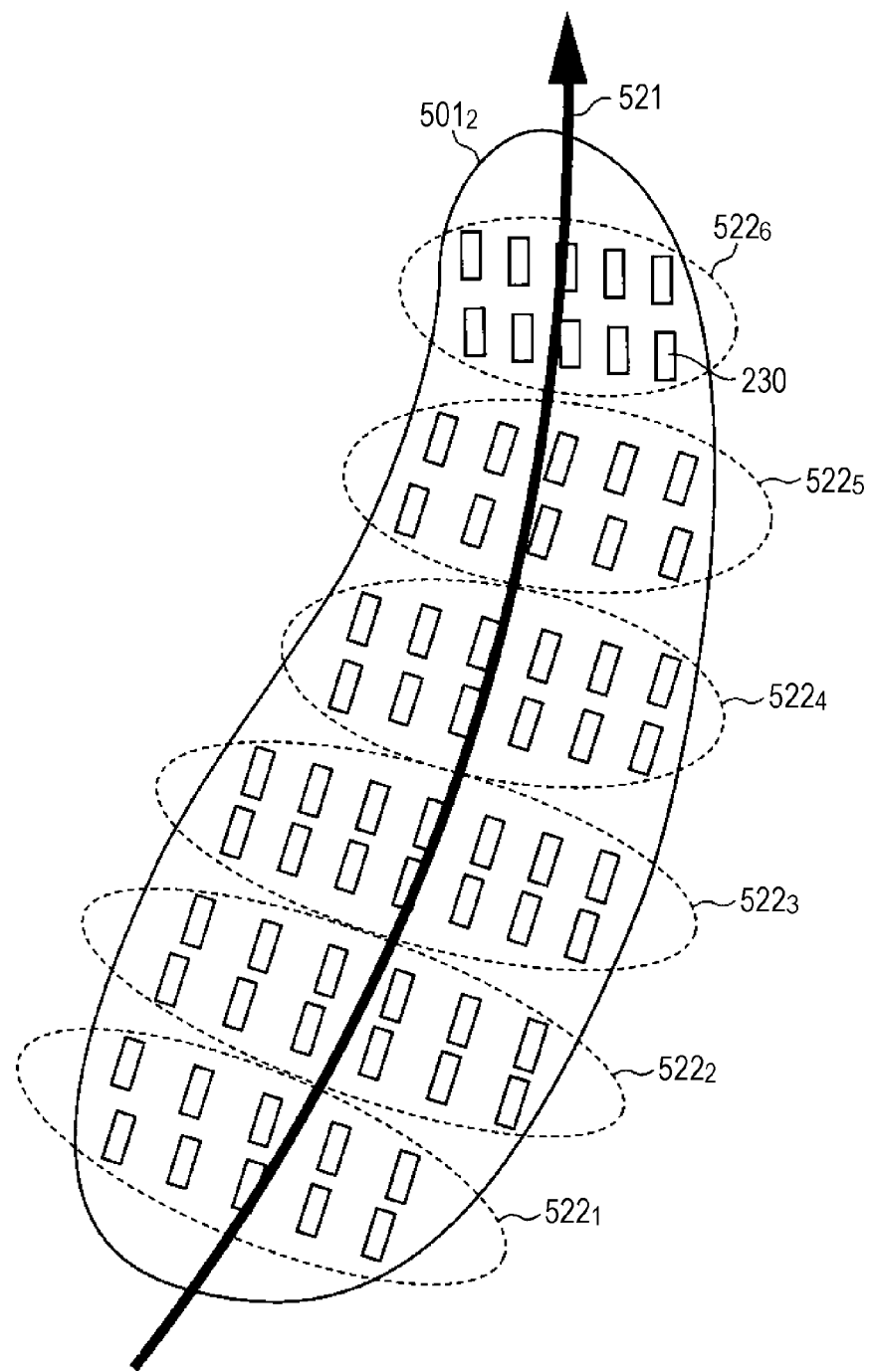
FIG. 8 is a diagram illustrating an exemplary subblock layout according to the second embodiment.

FIG. 8 which corresponds to FIG. 5 is a diagram illustrating an exemplary subblock layout in the block $501_2$ which is present in the left-cheek-bone outer portion.

As illustrated in FIG. 8, many massage elements 230 are disposed in the block $501_2$. These many massage elements 230 are grouped according to their sequence starting from the upstream side of a lymph discharge direction 521 (lower side in FIG. 8) into first to sixth subblocks $522_1$ to $522_6$. A group of massage elements 230 in each of the subblocks 522 is referred to as a "piezoelectric element matrix" when appropriate.

FIGS. 9A to 9F illustrate an example of an operation pattern which is specified in the block information table 510 (see FIG. 7) as the operation pattern 514 corresponding to the block $501_2$. FIGS. 9A to 9F illustrate periods in which pinching massage is applied to skin in the first to sixth subblocks $522_1$ to $522_6$ (see FIG. 8), respectively. In each of FIGS. 9A to 9F, the horizontal axis represents time, and the vertical axis represents voltage applied to the massage elements 230.

As illustrated in FIGS. 9A to 9F, voltage is first applied to the piezoelectric element matrix (massage elements 230) in the first subblock $522_1$. That is, pinching massage is applied to skin in the first subblock $522_1$. The time T of a massage period $523_1$ for the first subblock $522_1$ is, for example, 0.2 seconds. Then, at a timing of the middle of the massage period $523_1$ for the first subblock $522_1$, that is, at a timing at which the time T/2 has elapsed, an operation similar to that for the first subblock $522_1$ is started in the second subblock $522_2$. A similar operation is performed subsequently in the third to sixth subblocks $522_3$ to $522_6$.

That is, an area in which pinching massage is applied to skin is switched from a subblock 522 on the upstream side in the lymph discharge direction 521 to a subblock 522 on the downstream side in the lymph discharge direction 521 in such a manner that the massage period for a subblock 522 overlaps that for the next subblock 522. Such an operation pattern is described in the block information table 510 as an operation pattern in which pinching massage is applied sequentially from the downstream side to the upstream side.

Such movement of the massage area functions as an operation similar to horizontal-direction massage applied by using fingers sliding on skin in the lymph discharge direction 521. Therefore, the massaging apparatus 100 operates the massage elements 230 in accordance with the block information table 510, thereby prompting discharge of lymph under skin and improving skin condition for each of the blocks 510.

The length of the massage period 523 may be even for all of the blocks 501, or may differ among the blocks 501 or among the subblocks 522. The voltage applied to the massage elements 230 in each of the massage periods 523 may be even for all of the blocks 501, may differ among the blocks 501 or among the subblocks 522, or may differ among portions in a subblock 522.

In description which will be made below, an operation of moving a massage area from the most upstream side to the most downstream side in the lymph discharge direction in one block once is regarded as one massage operation unit (cycle).

FIG. 10 is a diagram illustrating an exemplary control rule table.

As illustrated in FIG. 10, a control rule table 530 describes identification information 532 and massage pattern information 533 of a massage pattern in association with an oxygen saturation level 531 (skin condition).

The oxygen saturation level 531 is information obtained by classifying skin condition in accordance with its oxygen saturation level. The massage pattern is an operation pattern for the massage elements 230 which corresponds to massage with predetermined intensity. Specifically, the massage pattern is information for specifying how many cycles (including zero cycle) of operation is to be performed in a block.

For example, an oxygen saturation level 531 of "slightly insufficient" is associated with a massage pattern having identification information 532 of "II". As the massage pattern information 533 of the massage pattern, "normal massage, a three-cycle massage using a piezoelectric element matrix" is specified.

This massage pattern specifies that multiple massage elements 230 included in a block 501 are operated for three cycles with the operation pattern 514 (see FIG. 7) specified in the block information table 510. This massage pattern corresponds to relatively low-intensity massage. This is because the lymph retention level indicated by the oxygen saturation level 531 of "slightly insufficient" is relatively low and gentle massage is enough. This oxygen saturation level 531 corresponds to, for example, skin condition of an oxygen saturation of 95% to 98%.

For example, an oxygen saturation level 531 of "seriously insufficient" is associated with a massage pattern having identification information 532 of "IV". As the massage pattern information 533 of the massage pattern, "intense massage, continue applying massage by using a piezoelectric element matrix, and stop when the oxygen saturation level is improved or when a ten-cycle massage is applied" is specified.

This massage pattern specifies that multiple massage elements 230 included in a block 501 are operated at most for ten cycles with the operation pattern 514 (see FIG. 7) specified in the block information table 510. This massage pattern corresponds to relatively high-intensity massage. This is because the lymph retention level indicated by the oxygen saturation level 531 of "seriously insufficient" is relatively high and intense massage is necessary. This oxygen saturation level 531 corresponds to, for example, skin condition of an oxygen saturation of less than 85%.

The massage pattern having the identification information 532 of "IV" also specifies that the massage is to be stopped regardless of the number of cycles when the oxygen saturation level is improved (to an oxygen saturation level of "insufficient") after the massage is started. This is because the degree of improvement in the oxygen saturation even for massage having the same intensity depends on individuals, and massage is to be prevented from being excessively applied due to the differences among individuals.

The control rule table 530 having a different description may be prepared for each block, that is, for each face portion. The control rule table 530 may be stored in a server or the like with which communication is performed through the Internet or the like. This configuration enables a user to receive various latest types of massage. In particular, for a user who easily gets edema, such as an artificial dialysis patient, if an aesthetician, a doctor, or the like studies an optimal massage pattern and stores it every time he/she makes diagnosis, edema is efficiently eliminated.

The operation determination unit 320 in FIG. 6 is connected to each of the first to Mth skin condition sensors $220_1$ to $220_M$ and the first to Nth massage elements $230_1$ to $230_N$ through the cable 400 (see FIG. 2) connecting the controller 300 to the sheet device 200, and through the signal lines (not illustrated) embedded in the sheet device 200.

That is, the operation determination unit 320 is capable of outputting control signals to the skin condition sensors 220 so as to control their operations, and is capable of receiving detected values outputted from the skin condition sensors 220. The operation determination unit 320 is also capable of outputting control signals to the massage elements 230 so as to control their operations.

The operation determination unit 320 obtains the skin condition (oxygen saturation level) of each of the blocks 501 on the basis of detection results (light information) received from the skin condition sensors 220. The operation determination unit 320 refers to the block information table 510 (see FIG. 7) and the control rule table 530 (see FIG. 10), and determines an operation which is to be performed by the massage elements 230 on the basis of the obtained skin condition. That is, the operation determination unit 320 determines an operation which is to be performed by the massage elements 230 so that higher-intensity lymph massage is applied for a block 501 having a higher lymph retention level.

The controller 300 includes, for example, a central processing unit (CPU), a storage medium such as a read only memory (ROM) storing control programs, and a work memory such as a random access memory (RAM), which are not illustrated. In this case, the function of each unit in the controller 300 is performed with the CPU executing the control programs.

The controller 300 includes a power supply unit and an operation unit such as a key switch, which are not illustrated. The power supply unit supplies power for operating the CPU and the sheet device 200. The operation unit receives various operations including an operation for starting massage, from a user.

This configuration enables the massaging apparatus 100 to massage each portion of skin with adequate intensity according to the skin condition of the portion.

Operation of Massaging Apparatus

An operation performed by the massaging apparatus 100 will be described.

FIG. 11 is a flowchart of an exemplary operation performed by the massaging apparatus 100.

When a user who wears the sheet device 200 on his/her face transmits an instruction to start the operation of the massaging apparatus 100, the massaging apparatus 100 starts a process described below.

In step S1100, each of the first to Mth skin condition sensors $220_1$ to $220_M$ detects skin condition (light information) before massage, and outputs the detection result to the operation determination unit 320. The operation determination unit 320 calculates an oxygen saturation of blood from the received skin condition for each of the skin condition sensors 220, and calculates an average (hereinafter referred to as a "block detection value") of the oxygen saturations of blood for each of the blocks 501. In the calculation of an oxygen saturation, the operation determination unit 320 refers to, for example, a table which describes light information and an oxygen saturation associated with each other and which is stored in the information storage unit 310 in advance. The reason why an average is used is to obtain data having higher reliability. The operation determination unit 320 records the calculated averages as initial block detection values.

In step S1200, the operation determination unit 320 determines a massage pattern on the basis of the initial block detection value for each of the blocks 501. That is, the operation determination unit 320 determines an oxygen saturation level 531 corresponding to the initial block detection value, and obtains a massage pattern corresponding to the determined oxygen saturation level 531 (see FIG. 10). In the determination of an oxygen saturation level 531, the operation determination unit 320 refers to, for example, a table in which an oxygen saturation and the oxygen saturation level 531 are associated with each other and which is stored in the information storage unit 310 in advance. Then, the operation determination unit 320 causes the massage elements 230 in each of the blocks 501 to start an operation with the corresponding operation pattern 514 (see FIG. 7).

In step S1300, the operation determination unit 320 selects one block from the blocks 501 for which massage is being applied. The operation determination unit 320 regards one period in which the process performs steps S1300 to S1800 (described below), as one process period. This process period is conceptually different from one cycle described above.

In step S1400, the operation determination unit 320 determines whether or not an end condition is satisfied for the selected block 501.

The end condition is a condition with which the massage operation is to be ended and which is indicated by the massage pattern determined in step S1200. For example, assume that a massage pattern of "normal massage, a three-cycle massage using a piezoelectric element matrix" is determined. In this case, the end condition is that the operation corresponding to the operation pattern has been performed for three cycles.

For example, assume that a massage pattern of "intense massage, continue applying massage by using a piezoelectric element matrix, and stop when the oxygen saturation level is improved or when a ten-cycle massage is applied" is determined. In this case, the end condition is that at least one of a condition that the operation corresponding to the operation pattern has been performed for ten cycles and a condition that the oxygen saturation level is improved is satisfied.

Whether or not the oxygen saturation level is improved may be determined by comparing the block detection value detected in the current process period with a predetermined threshold.

If the end condition for the selected block 501 is satisfied (YES in step S1400), the operation determination unit 320 causes the process to proceed to step S1500. If the end condition for the selected block 501 is not satisfied (NO in step S1400), the operation determination unit 320 causes the process to proceed to step S1600.

The case in which the end condition is not satisfied is, in other words, a state in which massage has not been sufficiently applied. The case in which the end condition is satisfied is, in other words, a state in which massage has sufficiently applied and in which massage has not been excessively applied.

In step S1500, the operation determination unit 320 ends the massage operation for the selected block 501, and causes the process to proceed to step S1600.

In step S1600, the operation determination unit 320 determines whether or not a block 501 for which massage is being applied and which has not been selected is present in the current process period. If an unselected block 501 for which massage is being applied is present (YES in step S1600), the operation determination unit 320 causes the process to proceed to step S1700. If no unselected blocks 501 for which massage is being applied are present (NO in step S1600), the operation determination unit 320 causes the process to proceed to step S1800.

In step S1700, the operation determination unit 320 selects one block from the unselected blocks 501 for which massage is being applied, and causes the process to proceed to step S1400.

In step S1800, the operation determination unit 320 determines whether or not a block 501 for which massage is being applied is present. If a block 501 for which massage is being applied is present (YES in step S1800), the operation determination unit 320 returns the process back to step S1300. If no blocks 501 for which massage is being applied are present (NO in step S1800), the operation determination unit 320 ends the process.

The above-described operation enables the massaging apparatus 100 to apply massage for an adequate number of cycles (time length) according to the skin condition for each of the blocks 501.

Regardless of the oxygen saturation level, the operation determination unit 320 may stop massage using the massage elements 220 if the degree of a change in the oxygen saturation after the massage starts reaches a predetermined threshold. This prevents massage from being applied excessively due to the differences among individuals in the degree of an increase in oxygen saturation for massage. Whether or not the degree of a change in oxygen saturation reaches the predetermined threshold may be determined, for example, by comparing the threshold with the difference between the recorded initial block detection value and a block detection value detected in each process period.

The operation determination unit 320 may monitor a change in oxygen saturation for each block 501. When the oxygen saturation sharply increases or decreases in a block 501, the operation determination unit 320 may stop the massage for the block 501.

The operation determination unit 320 may also monitor a change in oxygen saturation for blocks 501 for which massage has been stopped. When a predetermined condition is satisfied, the operation determination unit 320 may restart massage. The predetermined condition is, for example, that the oxygen saturation level is degraded.

Effect of Massaging Apparatus

As described above, the massaging apparatus 100 according to the second embodiment enables massage to be applied with adequate intensity to a necessary portion such as a portion in which edema occurs, without a user determining which part of skin is to undergo massage with which intensity level. That is, the massaging apparatus 100 according to the second embodiment efficiently achieves improvement in skin condition.

The massaging apparatus 100 according to the second embodiment enables massage to be applied to skin without using both hands of a user. Therefore, the user may perform other tasks and operations while using the massaging apparatus 100. Further, the massaging apparatus 100 according to the second embodiment may prevent massage from being applied, for example, mainly to a face portion on the dominant hand side.

Adoption of Other Skin Information

The massaging apparatus 100 may determine an operation which is to be performed by the massage elements 230, by using the skin condition sensors 220 detecting, from skin, various types of information which are other than an oxygen saturation of blood and which represent the degree of necessity for massage. Examples of skin information representing the degree of necessity for massage include a blood flow volume, a tensile strength, a temperature, a blood pressure, the amount of water, the amount of sebum, and a color tone of skin, and the degree of muscular tension under skin. The intensity with which massage is to be applied for each detection value may be determined through an empirical rule, an experiment, or the like.

For example, when each of the skin condition sensors 220 includes a blood flow sensor which detects a blood flow value, a blood flow sensor described, for example, in "*Jyoji Keitai Kano-na Cho-kogata Reza Ketsuryukei* (Wearable Laser Blood Flowmeter)", Takanori Kiyokura, Shinji Mino, Junich Shimada, NTT Gijutsu Journal (NTT Technical Review), 2005. 11, Nippon Telegraph and Telephone Corporation (NTT Microsystem Integration Laboratories), PP. 25-27, may be employed. Among a laser diode and a phototransistor which constitute such a blood flow sensor, an organic LED device which is produced by printing and which uses a high-molecular polymer described, for example, in Japanese Unexamined Patent Application Publication No. 2009-48837 may be employed as the laser diode. An organic phototransistor which uses a polymer thin-film transistor and which is described, for example, in Japanese Unexamined Patent Application Publication No. 2007-300112 may be employed as the phototransistor.

For example, each of the skin condition sensors 220 which includes a color tone sensor may detect skin color, thereby detecting dark rings under the eyes or skin of muddiness. The massage elements 230 apply massage with intensity according to the presence or absence of the dark rings under the eyes or the skin of muddiness and the degree of their color. Thus, the massaging apparatus 100 may improve skin condition including the dark rings under the eyes or the skin of muddiness. In this case, as the color tone sensor, a color tone sensor described, for example, in "*Yuki Satsuzou Debaisu no Kenkyu Doko* (Research Trend in Organic Imaging Device)", Satoshi Aihara, Misao Kubota, NHK STRL R&D, No. 132, NHK Science & Technology Research Laboratories, March 2012, PP. 4-11, may be employed.

For example, the skin condition sensors 220 may measure the degree of tension (myoelectric potential or muscular stiffness) of muscles of facial expression, thereby detecting a downward-slanting corner of the mouth or a downward-slanting corner of an eye, or the state of eye opening due to fatigue of the muscles of facial expression. The massage elements 230 apply massage for causing the corner of the mouth or the corner of an eye to be raised or causing the eye to open more widely, in accordance with the measured degree of tension of the muscles of facial expression. Thus, the massaging apparatus 100 may improve skin condition related to the muscles of facial expression. For example, as the skin condition sensors 220 which measure muscular stiffness, a piezoelectric element described in Japanese Unexamined Patent Application Publication No. 3-236289 may be employed. In this case, the muscular stiffness level of each portion may be detected from the magnitudes of displacements of piezoelectric elements obtained when a certain voltage is applied.

The massaging apparatus 100 may determine an operation which is to be performed by the massage elements 230, on the basis of the combination of multiple types of information representing skin condition.

Further, the massaging apparatus 100 may use information other than a change in oxygen saturation of blood, as skin information for preventing excessive massage. For example, the massaging apparatus 100 may detect a skin temperature. When the skin temperature exceeds a predetermined threshold such as 42° C., the massaging apparatus 100 may stop the operation of massage regardless of the number of cycles for which massage has been applied.

In this case, the sheet device 200 includes a temperature sensor which detects a skin temperature, for example, for each block or for each group of adjacent blocks and which outputs the detection result to the operation determination unit 320. As the temperature sensor, for example, a temperature sensor in which an organic molecule layer of an organic thin film transistor is formed of a phthalocyanine nanosized structure aggregate may be employed (for example, see International Publication No. 2013/151128).

Use of Outside Information in Combination

The massaging apparatus 100 may determine an operation which is to be performed by the massage elements 230, by using information other than skin information (hereinafter referred to as "outside information"), such as a temperature and a humidity, in combination. In this case, the massaging apparatus 100 includes an outside information acquisition unit which acquires outside information. The operation determination unit 320 refers to the control rule table including outside information as a condition for selecting a massage pattern, thereby determining an operation which is to be performed by the massage elements 230, on the basis of the acquired outside information.

FIG. 12 which corresponds to FIG. 10 is a diagram illustrating another exemplary control rule table. Portions corresponding to those in FIG. 10 are designated with identical reference numerals, and will not be described. In this example, the massage pattern information of each of the massage patterns is managed as another information by the information storage unit 310 so as to be associated with the identification information 532 of the massage pattern.

As illustrated in FIG. 12, in a control rule table 530a, each of the oxygen saturation levels 531 is associated with multiple outside information descriptions 534a. The control rule table 530a describes a combination of the oxygen saturation level 531 and the outside information description 534a which is associated with the identification information 532 of a massage pattern.

For example, a combination of the oxygen saturation level 531 of "slightly insufficient" and outside information descriptions 534a of temperature "20° C.-26° C." and temperature "<20° C." is associated with the massage pattern having the identification information 532 of "II". That is, this condition is associated with the massage pattern information 533 of "normal massage, a three-cycle massage using a piezoelectric element matrix" (see FIG. 10).

In contrast, for the same oxygen saturation level 531 of "slightly insufficient", a combination of the oxygen saturation level 531 and outside information description 534a of temperature "≥27° C." and humidity "≥80%" is associated with a massage pattern having identification information 532 of "I". That is, the condition is associated with massage pattern information 533 of "no massages, only continue measuring an oxygen saturation" (see FIG. 10).

Thus, in the control rule table 530a, the higher a temperature and a humidity are, the lower intensity with which massage is applied (including the case in which no massage is applied) is.

For example, when the temperature and the humidity are relatively high, the circulation of lymph and blood is typically improved over time, resulting in low necessity for massage. Therefore, the operation determination unit 320 refers to the control rule table 530a, and determines an operation which is to be performed by the massage elements 230, on the basis of not only skin condition but also the outside information, enabling the massaging apparatus 100 to apply further adequate massage.

As the outside information which is a source for determining an operation which is to be performed by the massage elements 230, the massaging apparatus 100 may use various other types of information which influence skin condition, such as atmospheric pressure, ultra violet (UV) absorbance, an intake of salt, alcohol, water, and potassium taken by a user, and the amount of exercise performed by a user.

The control rule table 530a having different description may be prepared for each block, that is, for each face portion.

Adoption of Other Massage

The massaging apparatus 100 may cause the massage elements 230 to apply another type of massage other than pinching massage, such as electrical stimulation or pressing. When electrical stimulation for muscles is employed as massage, an electrical muscle stimulation (EMS) element whose principle is disclosed, for example, in Japanese Unexamined Patent Application Publication No. 4-312472 may be employed as a massage element 230. In this case, the above-described block may be set for each muscle. EMS elements are disposed on both of the ends of a block in such a manner that the polarity on one end is the reverse polarity of that on the other end.

When muscle strength is built up, circulation of lymph and blood or the like is also improved. Therefore, this massaging apparatus 100 also efficiently achieves improvement in skin condition.

Other Modified Embodiments

Some or all of the functions of the controller 300 in the second embodiment described above may be deployed in an apparatus used mainly for another function, such as a cellular phone.

The above-described functions may be deployed in a server on a network. That is, some functions of the massaging apparatus 100 may be used as cloud service. In this case, the operation determination unit 320 needs to include at least a communication unit.

The massaging apparatus 100 may be applied to a sheet which also covers portions to positions behind the ears and a portion to a position near the collarbone. In addition, the massaging apparatus 100 may be applied to a cylindrical sheet covering another portion of the body, such as a calf.

In the massaging apparatus 100, each block may be provided with an operation determination unit 320 which performs operations for the block. In this case, the operation determination unit 320 may be a comparison circuit, for example, which compares an output signal from a skin condition sensor 220 with a predetermined threshold and which outputs the comparison result as a control signal for the massage elements 230.

A massage element which is an element consuming power, such as a piezoelectric element, inevitably emits heat. A heat-insulating layer or the like for reducing radiation of this heat may be provided on the surface or the like of the sheet. This configuration enables massage to be applied while the user skin is warmed, enhancing the effect of massage.

The massaging apparatus according to the present disclosure includes a sheet attachable to skin, a skin condition sensor included in the sheet, and a massage element included in the sheet. The massage element is operated based on a detection result obtained by the skin condition sensor.

In the above-described massaging apparatus, the skin condition sensor may detect information related to skin condition including at least one of a blood oxygen saturation of the skin, a blood flow volume of the skin, a tensile strength of the skin, a temperature of the skin, a blood pressure of the skin, the amount of water of the skin, the amount of sebum of the skin, a color tone of the skin, and a degree of muscular tension under the skin. The massage element may apply massage including at least one of pinching massage and electrical stimulation to the skin.

In the above-described massaging apparatus, a plurality of skin condition sensors including the skin condition sensor may be disposed in the sheet. A plurality of massage elements including the massage element may be included in the sheet, and may be operated based on a detection result obtained by the plurality of skin condition sensors.

The above-described massaging apparatus may further include an operation determination unit. Each of a plurality of areas, into which the sheet is divided, may include one or more skin condition sensors among the plurality of skin condition sensors and one or more massage elements among the plurality of massage elements. For each of the plurality of areas, the operation determination unit may determine an operation which is to be performed by the one or more massage elements included in the area, based on a detection result obtained by the one or more skin condition sensors included in the area.

In the above-described massaging apparatus, each of the plurality of skin condition sensors may detect the information related to the skin condition indicating a lymph retention level of the skin. For the area in which the lymph retention level is higher, the operation determination unit may operate the one or more massage elements included in the area with higher intensity.

The above-described massaging apparatus may further include an information storage unit stores an association in which each of the plurality of areas is associated with an operation pattern for the one or more massage elements included in the area. Each of the plurality of skin condition sensors may detect the information related to the skin condition indicating a lymph retention level of the skin. The operation pattern may move a massage area to which the massage element applies the massage in a direction in which lymph under the skin is discharged.

In the above-described massaging apparatus, the massage element stops massage if a degree of a change in skin condition reaches a predetermined threshold after the massage is started.

The above-described massaging apparatus may further include an outside information acquisition unit that acquires outside information. The operation determination unit may determine an operation which is to be performed by the one or more massage elements included in the area, based on the acquired outside information.

The massage method according to the present disclosure includes, by using a skin condition sensor included in a sheet attachable to skin, detecting information related to condition of the skin, and operating a massage element based on a detection result obtained by the skin condition sensor. The massage element is included in the sheet.

The present disclosure is useful for a massaging apparatus and a massage method which achieve improvement in skin condition more efficiently.

What is claimed is:

1. A massaging apparatus comprising:
a sheet that includes an area including subareas and is attachable to skin of a user including a part of the skin, the area corresponding to the part;
skin condition sensors that are included in the area and output detection results indicating retention levels of lymph under the part;
piezoelectric elements that are included in the subareas and are adapted to apply an operation to discharge the lymph; and
a processor that determines the operation, based on the detection results and first information stored in a memory, and causes the piezoelectric elements to perform the operation,
wherein the piezoelectric elements include a first piezoelectric element, a second piezoelectric element, and a third piezoelectric element,
wherein the first information includes information indicating that the first piezoelectric element is activated during a first period, the second piezoelectric element is activated during a second period, and the third piezoelectric element is activated during a third period,
wherein the subareas includes a first subarea including the first piezoelectric element, a second subarea including the second piezoelectric element, and a third subarea including the third piezoelectric element,
wherein the second subarea is provided between the first subarea and the third subarea, the first subarea touches the second subarea, the third subarea touches the second subarea, the first subarea and the second subarea having no overlap, the first subarea and the third subarea having no overlap, and the second subarea and the third subarea having no overlap,
wherein the lymph is adapted to be discharged from a portion under the first subarea to a portion under the third subarea through a portion under the second subarea,
wherein the first period is a continuous time, the second period is a continuous time, and the third period is a continuous time,
wherein a start time of the first period precedes a start time of the second period, a start time of the second period precedes a start time of the third period, an end time of the first period precedes an end time of the second period, and an end time of the second period precedes an end time of the third period,
wherein the sheet has a three-dimensional shape and configured to cover an entire face of the user except for openings for eyes and nostrils of the user,
wherein the sheet has elasticity and flexibility,
wherein the sheet is configured to maintain a contact with a skin surface of the entire face except for the openings for the eyes and the nostrils of the user due to a surface tension of the sheet, and
wherein a massage pattern of the piezoelectric elements is determined based on an outside temperature and an outside humidity.

2. The massaging apparatus according to claim 1, wherein, when an average level of the detection results indicates a lymph retention level for the area is higher, the processor causes the piezoelectric elements to perform the operation with higher intensity.

3. The massaging apparatus according to claim 1,
wherein the processor causes the piezoelectric elements to stop the operation by comparing an average level of the detection results with a predetermined threshold after the massage is started.

4. The massaging apparatus according to claim 1,
wherein the processor acquires outside information including the outside temperature and the outside humidity,
wherein the processor determines the operation based on the acquired outside information.

5. The massaging apparatus according to claim 1,
wherein each of the skin condition sensors includes a light emitter that emits a near infrared light to the part of the skin and a detector that detects a resulting light reflected from the part,
wherein each of the detection results is decided based on the resulting light, and
wherein each of the piezoelectric elements produces a displacement, according to a voltage, and the displacement is applied to the part to perform the operation.

6. The massaging apparatus according to claim 1,
wherein the second period partially overlaps with the first period, and
the third period partially overlaps with the second period, and
the first period and the third period do not overlap with another.

7. The massaging apparatus according to claim 1,
wherein the massage pattern is determined based on an oxygen saturation level of the skin surface of the user.

8. The massaging apparatus according to claim 1,
wherein the massage pattern is independently determined for each of the subareas.

9. A massage method comprising:
obtaining detection results, outputted by skin condition sensors, indicating retention levels of lymph under a part of a skin of a user, a sheet including an area having subareas, the sheet being attachable to the skin including the part, the area corresponding to the part, and the skin condition sensors being included in the area;
applying an operation to discharge the lymph using piezoelectric elements included in the subareas;
determining the operation, based on the detection results and first information stored in a memory; and
causing the piezoelectric elements to perform the operation,
wherein the piezoelectric elements include a first piezoelectric element, a second piezoelectric element, and a third piezoelectric element,
wherein the first information includes information indicating that the first piezoelectric element is activated during a first period, the second piezoelectric element is activated during a second period, and the third piezoelectric element is activated during a third period,
wherein the subareas includes a first subarea including the first piezoelectric element, a second subarea including the second piezoelectric element, and a third subarea including the third piezoelectric element,
wherein the second subarea is provided between the first subarea and the third subarea, the first subarea touches the second subarea, the third subarea touches the second subarea, the first subarea and the second subarea having no overlap, the first subarea and the third subarea having no overlap, and the second subarea and the third subarea having no overlap,
wherein the lymph is adapted to be discharged from a portion under the first subarea to a portion under the third subarea through a portion under the second subarea,
wherein the first period is a continuous time, the second period is a continuous time, and the third period is a continuous time,
wherein a start time of the first period precedes a start time of the second period, a start time of the second period precedes a start time of the third period, an end time of the first period precedes an end time of the second period, and an end time of the second period precedes an end time of the third period,
wherein the sheet has a three-dimensional shape and configured to cover an entire face of the user except for openings for eyes and nostrils of the user,
wherein the sheet has elasticity and flexibility,
wherein the sheet is configured to maintain a contact with a skin surface of the entire face except for the openings for the eyes and the nostrils of the user due to a surface tension of the sheet, and
wherein a massage pattern of the piezoelectric elements is determined based on an outside temperature and an outside humidity.

10. The massage method to claim 9,
wherein each of the skin condition sensors includes a light emitter that emits a near infrared light to the part of the skin and a detector that detect a resulting light reflected from the part,
wherein each of the detection results is decided based on the resulting light, and
wherein each of the piezoelectric elements produces a displacement, according to a voltage, and the displacement is applied to the part to perform the operation.

* * * * *